US006918304B2

(12) United States Patent
Fujii et al.

(10) Patent No.: US 6,918,304 B2
(45) Date of Patent: Jul. 19, 2005

(54) MATERIAL TESTING METHOD

(75) Inventors: Yusaku Fujii, Kiryu (JP); Takao Yamaguchi, Nitta-gun (JP)

(73) Assignee: Gunma University, Maebashi (JP)

( * ) Notice: Subject to any disclaimer, the term of this patent is extended or adjusted under 35 U.S.C. 154(b) by 26 days.

(21) Appl. No.: 10/725,464

(22) Filed: Dec. 3, 2003

(65) Prior Publication Data

US 2005/0097964 A1 May 12, 2005

(30) Foreign Application Priority Data

Nov. 11, 2003 (JP) ............................. 2003-381385

(51) Int. Cl.[7] .............................................. G01B 7/16
(52) U.S. Cl. ...................................................... 73/778
(58) Field of Search ........................ 73/778, 781, 788, 73/796, 797, 801

(56) References Cited

U.S. PATENT DOCUMENTS

| 3,803,906 | A | * | 4/1974 | Ross ............................ 73/805 |
| 3,901,074 | A | | 8/1975 | Douglas |
| 5,284,058 | A | | 2/1994 | Jones |
| 5,526,697 | A | * | 6/1996 | Tada et al. ............. 73/862.634 |
| 5,902,964 | A | * | 5/1999 | Solberg, Jr. et al. ............ 177/1 |
| 6,055,471 | A | * | 4/2000 | Ohsaku et al. ................. 701/37 |
| 6,324,915 | B1 | | 12/2001 | Potts |
| 6,573,897 | B1 | * | 6/2003 | Desbrun et al. ............. 345/473 |

FOREIGN PATENT DOCUMENTS

| EP | 0 893 669 A1 | 1/1999 |
| EP | 1 236 996 A1 | 9/2002 |
| JP | 3177681 B2 | 4/2001 |

OTHER PUBLICATIONS

JSME Mechanical Engineer's Handbook, Apr. 15, 1987 (New Edition) with English Abstract.
"A Method for Calibrating Force Transducers Oscillation Force," by Yusaku Fujii, Jul. 16, 2003, pp. 1259-1264.
Proposal for A Step Response Evaluation Method for Force Transducers, by Yusaku Fujii, Measurement Science and Technology, Aug. 11, 2003, pp. 1741-1746.

* cited by examiner

*Primary Examiner*—Max Noori
(74) *Attorney, Agent, or Firm*—Birch, Stewart, Kolasch & Birch, LLP

(57) ABSTRACT

The present invention aims to achieve accurate measurement and evaluation of mechanical properties of an object to be measured 1 without use of a force sensor. A weight 3 is attached to the object to be measured 1 to form a mass-spring system in which the object to be measured 1 serves as a spring element. Then vibration is applied to the mass-spring system to measure the inertial force acting on the weight 3 and the displacement of the weight 3 so that the mechanical properties of the object to be measured 1 will be evaluated based on the inertial force and displacement. A light wave interferometer 6 measures the displacement velocity of the weight 3 to calculate the inertial force from the acceleration determined by differentiating measured values of the displacement velocity of the weight 3 and calculate the displacement of the weight 3 by integrating the measured values of the displacement velocity of the weight 3.

8 Claims, 5 Drawing Sheets $a = dv / dt$ $x = \int v\, dt$ $F = M a$

MATERIAL TESTING METHOD

This Nonprovisional application claims priority under 35 U.S.C. § 119(a) on Patent Application No(s). 2003-381385 filed in Japan on Nov. 11, 2003, the entire contents of which are hereby incorporated by reference.

BACKGROUND OF THE INVENTION

1. Field of the Invention

The present invention relates to a material testing method for evaluating mechanical properties of objects to be measured.

2. Description of Related Art

This type of material testing method is designed to determine the magnitude of a force acting on an object to be measured and the amount of strain on the object to be measured so as to evaluate mechanical properties such as an elastic coefficient of the object to be measured based on the measured force and strain. In the conventional method, the force acting on the object to be measured is measured with a force sensor such as a load cell (for example, see JSME Mechanical Engineers' Handbook, B3, p 74, published by The Japan Society of Mechanical Engineers (JSME) on Apr. 15, 1987).

A calibration technique (static calibration method) for the detection output of a force sensor system for detecting static forces is already established. However, when a dynamic force is exerted on the force sensor, unique phenomena occur, such as a delay in the response of the output of the sensor and the change in the shape of the output of the sensor. In use of the force sensor, the dynamic response must be determined in terms of the whole sensing system, such as a force sensing system consisted of a force sensor, an amplifier and a digital multi-meter. In this case, even when the detection output of the force sensor system is calibrated by the static calibration method, the dynamic force cannot be measured accurately. Thus, when a force acting on an object to be measured changes, the accuracy of measurement cannot be guaranteed even if the force is measured with the force sensor, and this makes it difficult to evaluate the mechanical properties of the object to be measured accurately. Furthermore, it is usually difficult to synchronize the measurement of force using a force sensor and measurement of strain using a displacement sensor, because both the force sensor and the displacement sensor have some delay in their output and the deformation of the shape of output signal.

SUMMARY OF THE INVENTION

In view of the above point, it is an object of the present invention to provide a material testing method, which can ensure the accuracy of measurement of a force acting on an object to be measured so that the mechanical properties of the object to be measured can be accurately evaluated.

In order to solve the above problem, according to the invention, a weight is attached to an object to be measured to form a mass-spring system in which the object to be measured serves as a spring element. Then, vibration is applied to the mass-spring system, and the inertial force acting on the weight and the displacement of the weight are measured to evaluate the mechanical properties of the object to be measured based on the inertial force and displacement.

Upon vibration of the mass-spring system, the force exerted from the weight to the object to be measured and the force exerted from the object to be measured to the weight are equal in magnitude but opposite in direction according to the action-reaction law. Under the conditions in which the frictional force acting on the weight is negligible, the inertial force of the weight becomes equal to the force exerted from the object to be measured to the weight. For this reason, the force acting on the object to be measured can be measured with high precision from the inertial force of the weight. Further, since the weight is displaced according to the strain on the object to be measured, the amount of strain on the object to be measured can be determined with high precision from the displacement of the weight. Thus the mechanical properties of the object to be measured can be accurately evaluated based on the inertial force and displacement of the weight. Particularly, according to the present invention, the accuracy of evaluation of mechanical properties of an object to be measured under varying loads is improved dramatically compared to the conventional case using the force sensor.

The inertial force of the weight is equal to the product of the mass and acceleration of the weight. If a light wave interferometer, which launches measurement light at a reflecting part provided on the weight and measures the state of the reflected light from the reflecting part, is used, the displacement, velocity, and acceleration of the weight can be determined from the state of the reflected light, thereby calculating the inertial force of the weight accurately from the determined acceleration of the weight. In this case, since the inertial force and displacement of the weight can be measured by the light wave interferometer alone, it is cost efficient. And since the inertial force and displacement of the weight can be measured by the light wave interferometer alone, the synchronization of the measured values of the displacement, velocity, acceleration and inertial force of the weight are automatically guaranteed.

It is also desired that the weight be supported by a linear bearing to limit the motion of the weight to one degree of freedom. Particularly, if the weight is supported by a pneumatic linear bearing, the frictional force acting on the weight can be reduced to a minimum, so that the difference between the inertial force of the weight and the force acting on the object to be measured can be reduced as much as possible, thereby the accuracy of measurement is improved.

To apply vibration to the mass-spring system, an impulsive force may be applied to the weight. Alternatively, if an actuator is coupled to the object to be measured so that the actuator will apply vibration to the mass-spring system, vibration of any magnitude and waveform can be applied. This advantageously makes it possible to determine the responses of the object to be measured against arbitrary wave, such as arbitrary vibration with arbitrary amplitude and frequency. In this case, the displacement of the side of the object to be measured connected to the actuator must be measured to calculate the strain of the object.

DESCRIPTION OF THE PREFERRED EMBODIMENTS

Figure 1:
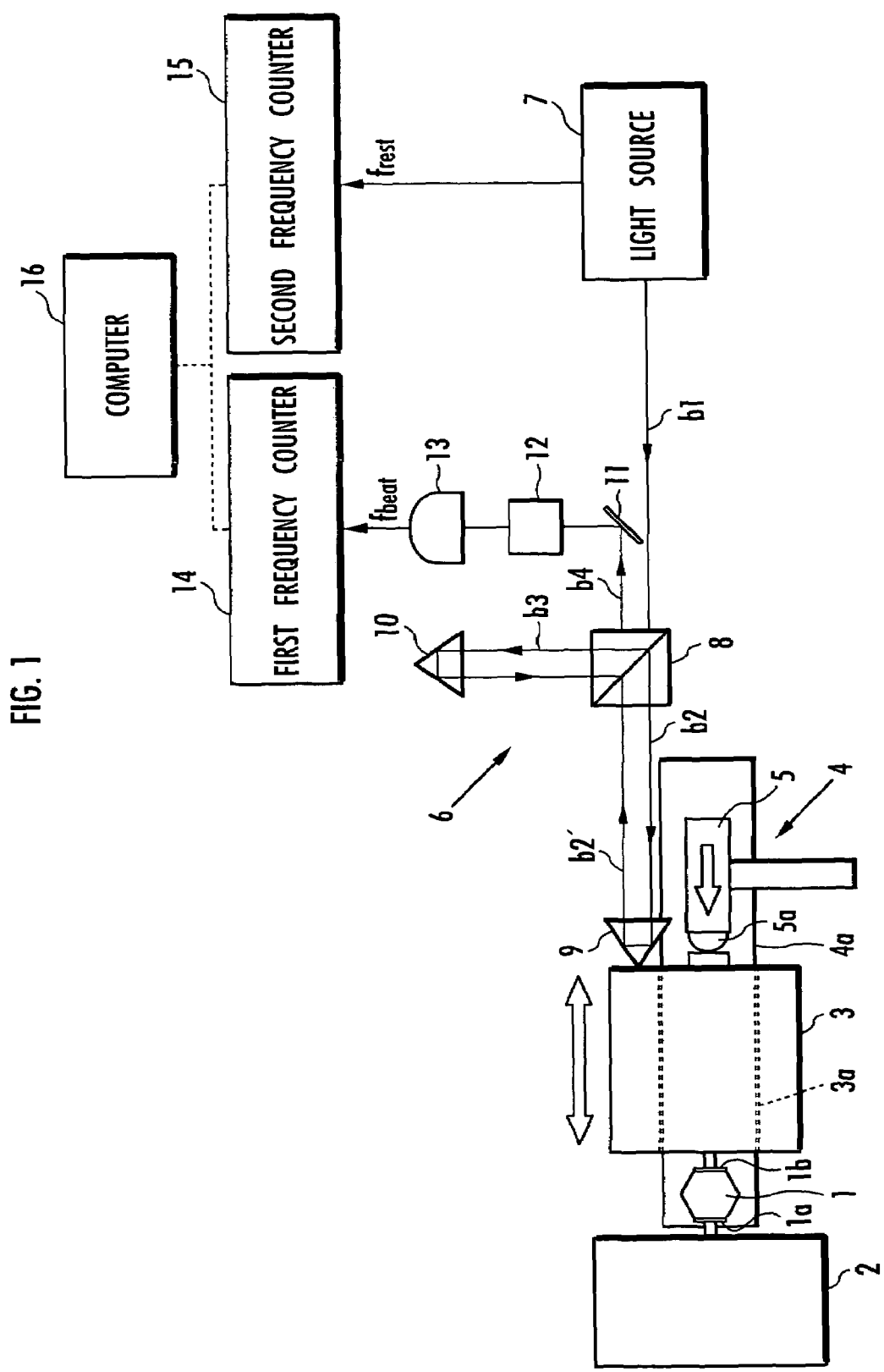
FIG. 1 is a block diagram showing the general structure of a first embodiment of a material testing apparatus in which the present invention is implemented.
Figure 2:
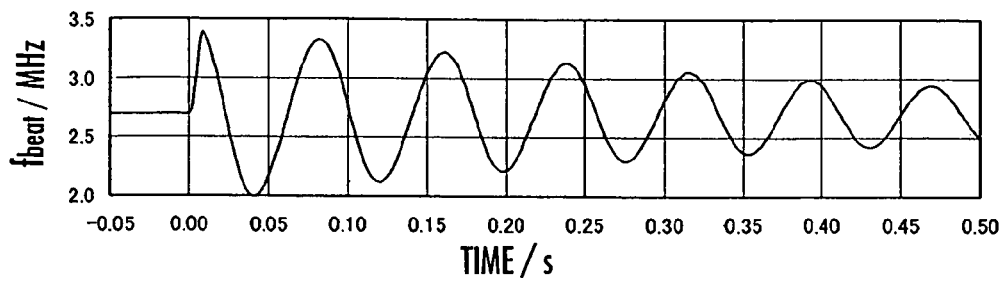
FIG. 2 shows graphs in which (a) indicates measured data on a beat frequency, (b) indicates the displacement velocity of a weight calculated from the measured data on the beat frequency, (c) indicates the displacement of the weight calculated from the displacement velocity, (d) indicates the acceleration of the weight calculated from the displacement velocity, and (e) indicates the inertial force of the weight calculated from the acceleration.
Figure 2:
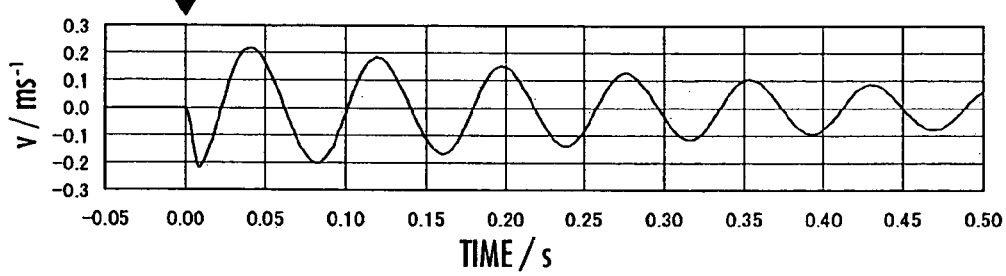
Figure 2:
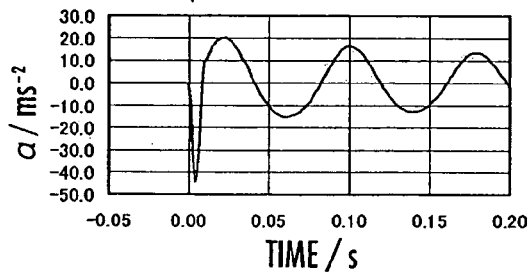
Figure 2:
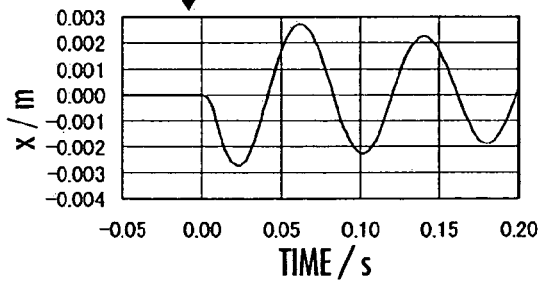
Figure 2:
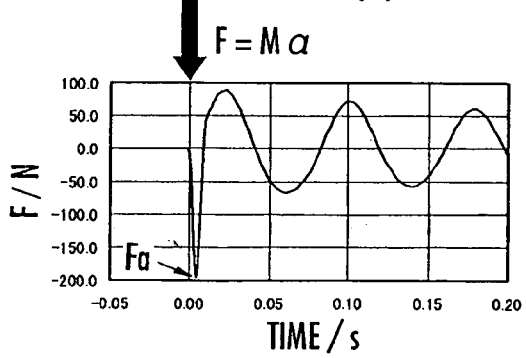
Figure 3:
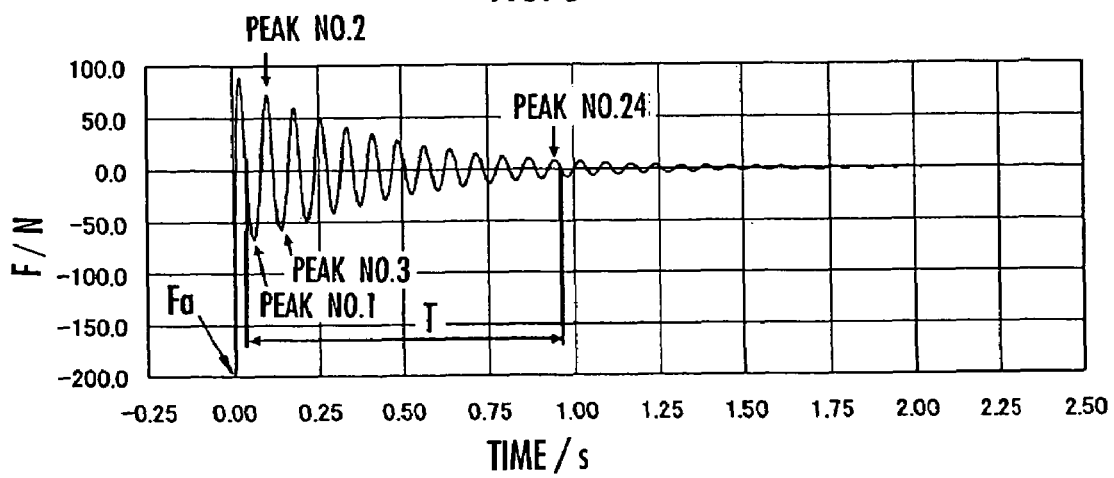
FIG. 3 is a graph showing variations in the inertial force of the weight until vibration ceases.
Figure 4:
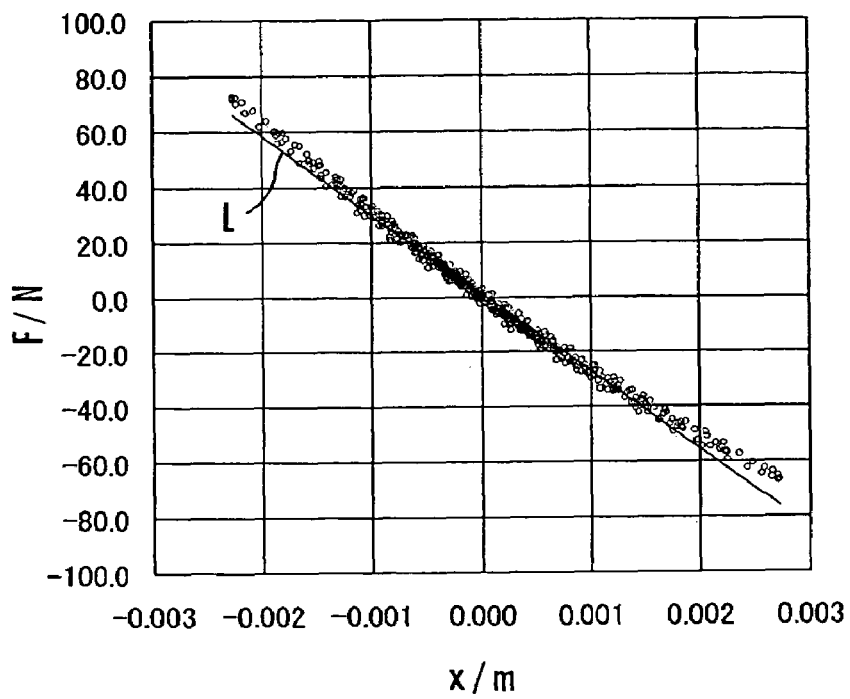
FIG. 4 is a graph showing the relationship between the inertial force and the displacement, and a regression line for the relationship.
Figure 5:
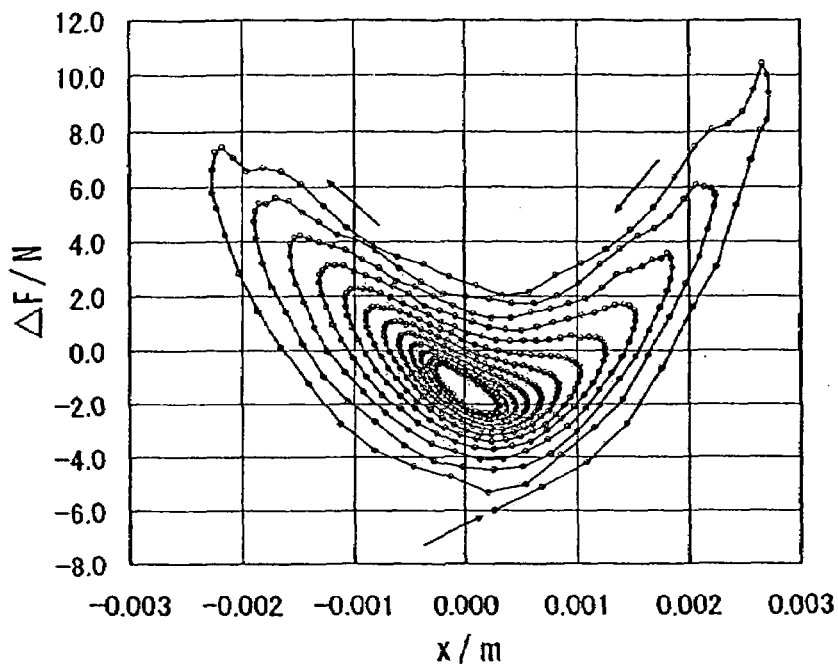
FIG. 5 is a graph showing the relationship between the deviation of the inertial force from the regression line and the displacement.
Figure 6:
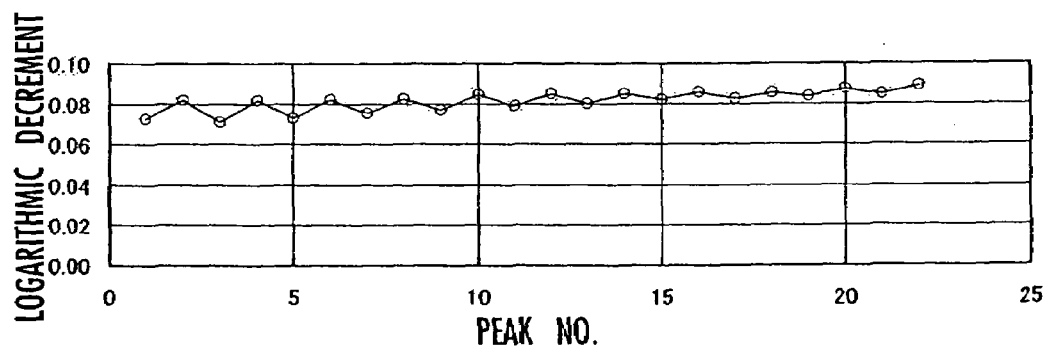
FIG. 6 shows graphs in which (a) indicates logarithmic decrement of the vibration and (b) indicates vibration cycle.
Figure 6:
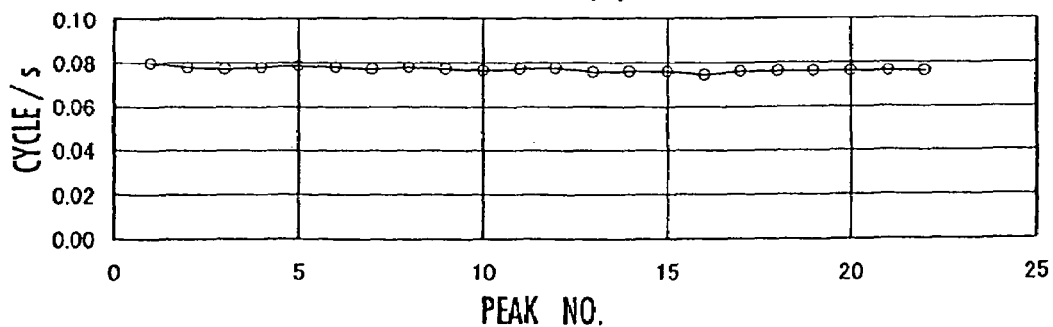
Figure 7:
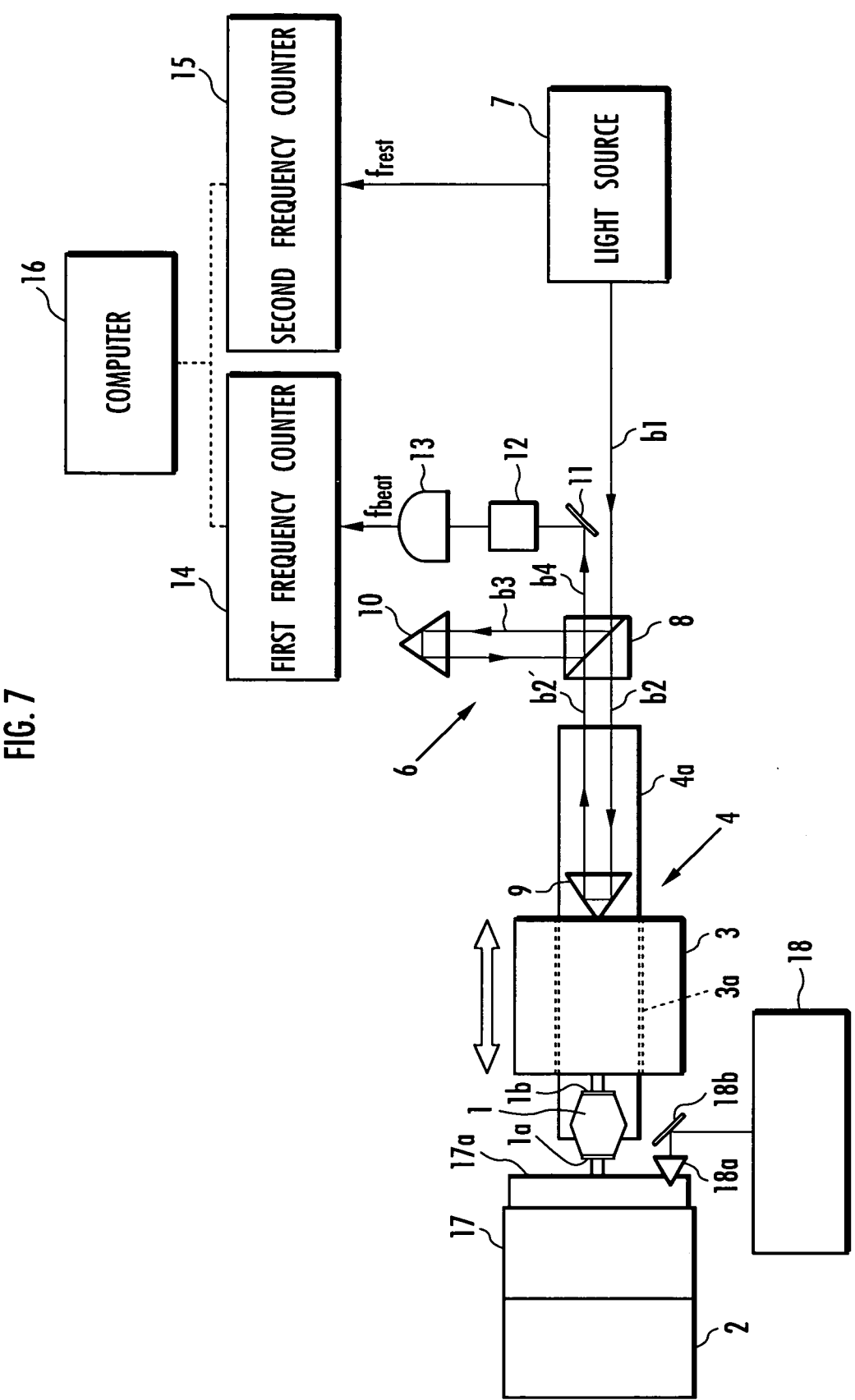
FIG. 7 is a block diagram showing the general structure of a second embodiment of a material testing apparatus.

Referring to FIGS. 1 through 7, embodiments of the present invention will now be described. FIG. 1 is a block diagram showing a first embodiment of a material testing apparatus in which the present invention is implemented. FIG. 2(a) is a graph showing measured data on a beat frequency. FIG. 2(b) is a graph showing the displacement velocity of a weight calculated from the measured data on the beat frequency. FIG. 2(c) is a graph showing the displacement of the weight calculated from the displacement velocity. FIG. 2(d) is a graph showing the acceleration of the weight calculated from the displacement velocity. FIG. 2(e) is a graph showing the inertial force of the weight calculated from the acceleration. FIG. 3 is a graph showing variations in the inertial force of the weight until vibration ceases. FIG. 4 is a graph showing the relationship between the inertial force and the displacement, and a regression line for the relationship. FIG. 5 is a graph showing the relationship between the deviation of the inertial force from the regression line and the displacement. FIG. 6(a) is a graph showing logarithmic decrement of the vibration. FIG. 6(b) is a graph showing vibration cycle. FIG. 7 is a block diagram showing the general structure of a second embodiment of a material testing apparatus.

Referring to FIG. 1, one end of an object to be measured 1 is fixed to a base 2 of the material testing apparatus and the other end thereof is fixed to a weight 3. Thus the object to be measured 1 and the weight 3 form a mass-spring system in which the object to be measured 1 serves as a spring element. Although the object to be measured 1 may be of any kind, the object to be measured 1 in the example shown in FIG. 1 is a damper in the form of a silicon rubber block with metal plates 1a and 1b bonded at both ends thereof. The metal plates 1a and 1b at both ends are fixed to the base 2 and the weight 3, respectively, with appropriate means such as screws.

The weight 3 is supported by a linear bearing 4 fixed to the base 2 so that the freedom of motion of the weight will be limited to the uniaxial horizontal motion. As the linear bearing 4, a pneumatic linear bearing with low frictional resistance, for example, Air Slide (trademark) of NTN Co. Ltd., is used. The linear bearing 4 has a linear guide part 4a to be inserted into a through-hole 3a formed in the weight 3 as a moving part, so that a compressed air layer is built up in a space between the inner circumference of the through hole 3a and the outer circumference of the guide part 4a throughout the through hole 3a. Thus the weight 3 is free to move linearly with extremely low frictional resistance in the direction of the axial line of the guide part 4a (hereinafter called the guide axial line). Although not shown, the compressed air is introduced from the guide part 4a, led from an outlet formed in the central portion of the guide part 4a, through an inner circumferential groove of the weight 3, into an inlet formed in the central portion of the weight 3, and supplied to the space through an inner pipe-line system of the weight 3. Although the air supply arrangement will become simpler if the compressed air is directly introduced into the weight 3 through an air supply tube, the compressed air is introduced from the guide part 4a to prevent an external force from the air supply tube from acting on the weight 3. Various types of pneumatic linear bearing including the type mentioned above are commercially available.

In the first embodiment, an impulsive force is applied by a hammer 5 to the weight 3 to apply vibration to the mass-spring system. The hammer 5 has a rubber pad 5a at its tip. Upon the application of vibration, the force exerted from the weight 3 to the object to be measured 1 and the force exerted from the object to be measured 1 to the weight 3 are equal in magnitude but opposite in direction according to the action-reaction law. Further, since the weight 3 is supported by the pneumatic linear bearing 4 and therefore the frictional force acting on the weight 3 is negligible, the inertial force F of the weight 3 becomes equal to the force exerted from the object to be measured 1 to the weight 3. In other words, it can be considered that the inertial force F of the weight 3 is a parameter that accurately represents the force acting on the object to be measured 1. It can also be considered that the displacement x of the weight 3 is a parameter that accurately represents the strain on the object to be measured 1. It can also be considered that the velocity v of the weight 3 is a parameter that accurately represents the strain rate on the object to be measured 1. As a result, the measurement of the inertial force F and the displacement x of the weight 3 enables an accurate evaluation of the mechanical properties of the object to be measured 1. It should be noted that the inertial force F of the weight 3 is determined by the equation F=M×a, where M is the mass of the weight 3 (including the masses of all the parts fixed to the weight) and a is the acceleration of the weight 3.

The material testing apparatus is provided with a light wave interferometer 6 for measuring the displacement velocity of the weight 3 in the direction of the guide axial line. The light wave interferometer 6 is well known in the art, and the outline of the light wave interferometer 6 will be described below. In the embodiment, the light wave interferometer 6 is provided with a light source 7 of Zeemann type Helium-Neon laser, which emits two kinds of linearly-polarized light having slightly different frequencies from each other. The two kinds of light b1 emitted from the light source 7 are separated by a polarization-beam-splitter 8 into measurement light b2 and reference light b3. The measurement light b2 is incident on a corner cube prism 9 as the reflecting part fixed to the weight 3. The incident light is reflected by the corner cube prism 9, and is incident on the polarization-beam-splitter 8 again. Since the direction of the light b2 is set parallel with the direction of the guide axial line, the reflected light b2' from the corner cube prism 9 becomes signal light causing a Doppler shift (a change in frequency due to the Doppler effect) according to the displacement velocity of the weight 3 in the direction of the guide axial line. On the other hand, the reference light b3 is incident on the polarization-beam-splitter 8 again from the polarization-beam-splitter beam-splitter 8 via a second corner cube prism 10, and is combined with the reflected light b2' to form interference light b4 producing beats of frequency corresponding to the difference in frequency between the reflected light b2' and the reference light b3. The interference light b4 is incident on a photodetector 13 from the polarization-beam-splitter 8 through a mirror 11 and a polarizing plate (e.g., Glan-Thompson prism) 12. The photodetector 13 converts the interference light b4 to an electrical signal according to the beat frequency fbeat of the interference light b4, and inputs the electrical signal into a first frequency counter 14. The first frequency counter 14 creates digital data representing the value of the beat frequency fbeat and sends the digital data to a computer 16. On the other hand, a built-in photodetector of the light source 7 creates an electrical signal of a reference frequency frest corresponding to the state of rest of the weight 3, and inputs the electrical signal into a second frequency counter 15. The second frequency counter 15 creates digital data representing the value of the reference frequency frest and sends the digital data to the computer 16. It should be noted that the displacement velocity v of the weight 3 in the direction of the guide axial line is determined by the equation v=$\lambda$air·(fbeat−frest)/2, where $\lambda$air is the refraction index of air.

In the embodiment, Advantest's MODEL R5363 is used for the frequency counters 14 and 15. This counter is designed to measure a frequency continuously and store 14000 measured values in memory. The measured values are read from the memory into the computer 16 through a GPIB bus. In order to achieve high-precision measurement, it is important to measure the frequency continuously. Further, instead of the frequency counters 14 and 15, a high-performance waveform recorder may be used to record electrical signals from the photodetector 13 and a built-in photodetector of the light source 7 so that the frequency and its variations over time will be determined from the recorded waveform. It enables more sophisticated measurement of frequencies.

The computer 16 includes the following functional means (means implemented by a program): means for sequentially calculating the displacement velocity v of the weight 3 in the direction of the guide axial line from the beat frequency fbeat and the reference frequency frest according to the above equation; means for sequentially calculating the displacement (position) x of the weight 3 in the direction of the guide axial line by integrating time-series values of the displacement velocity v; means for sequentially calculating the acceleration $\alpha$ of the weight 3 in the direction of the guide axial line by differentiating the time-series values of the displacement velocity v; and means for sequentially calculating the inertial force F of the weight 3 in the direction of the guide axial line from the calculated acceleration $\alpha$ and the prerecorded mass M of the weight 3. The computer 16 also includes as hardware storage means (not shown) such as a hard disk for storing and holding data on the calculated displacement velocity v, acceleration a, position x, and inertial force F in chronological order, and display means (not shown) such as a display and a printer for outputting these data as appropriate. The computer controls all the experimental setup, including frequency counters, through GPIB, AD converter and DA converter. Initiation of measurements of the two counters are done by means of the trigger signal generated by the computer. The initiation of the trigger signal is done by means of the light switch, which consists of LD (laser diode) and PD (photo diode), not shown. The light switch is detected the approach of the hammer to the weight. Also, the hammer may be swung under initiation by computer at starting of measurement, that is, swinging the hammer according to the beep from the computer.

When the action and reaction forces between the object to be measured 1 and the weight 3 exert a moment on the weight 3, the posture of the weight 3 can change, and it can cause various adverse effects. For example, the air layer between the weight 3 and the guide part 4a could be broken, and it result in increase of the frictional force, or the moment could be transmitted to the base 2 through the air layer to vibrate the components of the light wave interferometer 6. In such a case, the accuracy of measurements would be degraded. Therefore, an appropriate additional mass is attached to the weight 3 to make the straight line connecting the position of the gravity point of the weight 3 and the object to be measured 1 parallel with the guide axial line, thus preventing the moment from acting on the weight 3. Further, when considering the influence of vibration on the material testing apparatus, it is desired that a heavy table (e.g., a cast-iron table) fixed on the ground be used as the base 2 to make the entire structure stable, and vibration isolation measures be taken such as to support the light wave interferometer 6 in such a manner that is isolated from the base 2.

The following describes the results of a material test using the testing apparatus according to the first embodiment. The test was conducted on the aforementioned damper shown in FIG. 1 as the object to be measured 1 using a weight having a mass M of 4.5818 kg as the weight 3, and the measured data shown in FIG. 2 were obtained. In FIG. 2, the graph (a) shows the beat frequency fbeat, the graph (b) shows the displacement velocity v of the weight 3 in the direction of the guide axial line calculated from the beat frequency fbeat, the graph (c) shows the displacement x of the weight 3 calculated by integrating the values of the displacement velocity v, the graph (d) shows the acceleration a of the weight 3 calculated by differentiating the values of the displacement velocity v, and the graph (e) shows the inertial force F of the weight 3 calculated by multiplying the mass M of the weight 3 by the acceleration $\alpha$. The beat frequency fbeat varies, by the application of vibration, around a center or nominal frequency of about 2.6 MHz as a value when the weight 3 remains at rest (reference frequency frest). In FIG. 2(e), part of the inertial force indicated with Fa represents an impulsive force applied by the hammer 5, and this impulsive force vibrates the mass-spring system composed of the object to be measured 1 and the weight 3 at a frequency of about 13 Hz.

It should be noted that FIG. 2 shows the measured data at the beginning of the vibration and FIG. 3 shows data on the inertial force F until the vibration ceases. The following detailed analysis was made by selecting a period of about 0.92 sec. indicated with T in FIG. 3 during which 12 cycles and 24 peaks were included. In that analysis, the first half cycle including the first positive peak was eliminated from the analysis period T because the hammer 5 and the weight 3 could remain in contact with each other in the half cycle.

The relationship between the inertial force F and the displacement x found from the data on the inertial force F and the data on the displacement x in the analysis period T is shown in FIG. 4. In FIG. 4, a straight line L is a regression line for all the measured data in the analysis period T. It can be found that the object to be measured 1 is not an ideal elastic body because many measured data marked with circles in FIG. 4 are not perfectly on the regression line. Then, the relationship between the deviation $\Delta$F of the inertial force F from the regression line L and the displacement x is determined, and the results are shown in FIG. 5. A glance at FIG. 5 indicates the existence of an elastic hysteresis due to the damping properties of the object to be measured 1. In addition, FIGS. 6(a) and 6(b) show curves of logarithmic damping rates and vibration cycles at respective peaks in the analysis period T.

The following describes a second embodiment of a material testing apparatus shown in FIG. 7. In FIG. 7, members common to those in the first embodiment are given the same reference numerals to omit the description. A different point from the first embodiment is that an actuator 17 is provided between the base 2 and the object to be measured 1 in such a manner that the object to be measured 1 is coupled to the actuator 17. In this arrangement, the actuator 17 can apply vibration of any magnitude and waveform to the mass-spring system composed of the object to be measured 1 and the weight 3, and this makes it possible to determine the responses of the object to be measured against arbitrary wave, such as arbitrary vibration with arbitrary amplitude and frequency.

In this case, the displacement of the side of the object to be measured connected to the actuator must be measured to calculate the strain of the object. Therefore, in order to measure the displacement of a moving surface 17a of the actuator 17, a second light wave interferometer 18 is provided so that measurement light will be incident on a corner cube prism 18a fixed to the moving surface 17a through a mirror 18b. The optical interferometer 18 can be the same type to that used in the first embodiment. It can also be any other type, if at least it can measure the velocity, the position or the acceleration of the cube corner prism 18a. The strain on the object to be measured 1 is calculated from the displacement of the moving surface 17a and the displacement of the weight 3.

For material tests using the testing apparatus according to the first or second embodiment, various types of measurement equipment that cover the whole field of view can be provided in order to check the internal distribution of acceleration, velocity, and displacement of the object to be measured 1. The material testing method can also be combined with a numerical analysis method such as a finite element method. It enables a more sophisticated evaluation of mechanical properties of materials. Further, the use of a small weight, such as a weight of about 1 g, as the weight 3 makes it possible to carry out material tests on small forces, such as forces of about 1 $\mu$N or less. In this case, it is possible to test the mechanical properties of various materials used in a micromachine or nanomachine and the like.

Further, in the testing apparatuses according to the first and second embodiments, the direction of the motion of the weight 3 is horizontal, but the linear bearing 4 can be arranged vertically or slant so that the weight 3 can be moved in the direction of the vertical component. In this case, the gravitational component of the weight 3 is added to the force acting on the object to be measured 1. Furthermore, an actively-controlled-base system for actively controlling the attitude and the position of the weight 3 can be adopted to eliminate the need for the linear bearing 4.

In addition, in the above embodiments, the Zeemann type Helium-Neon laser oscillating at two frequencies slightly different from each other to emit two kinds of light is used as the light source 7 of the light wave interferometer 6, but any other light sources oscillating at a single frequency to emit one kind of light, such as stabilized semiconductor laser or Iodine-stabilized Helium-Neon laser, can be used. In this case, an acousto-optic element may be used to apply a frequency shift to one of the two light beams separated by the polarization-beam-splitter 8 so as to create two kinds of light slightly different in frequency, thus performing measurement in the same manner as in the above embodiments.

It should be noted that the Doppler shift of the reflected light b2' and the phase shift are two sides of the same coin. In other words, a Doppler frequency shift of light reflected from a moving object can be considered a phase shift corresponding to double the moving distance of the moving object. Therefore, there can also be used various other kinds of light wave interferometers, such as a light wave interferometer of interference fringe counting type for calibration of standard scales, designed to emit the measurement light from the light source oscillating at a single frequency to be incident on the reflecting part 9 of the weight 3, and to determine the phase shift of the reflected light from the reflecting part 9 of the weight 3 as the phase shift of interference fringes formed by combining the reflected light and the reference light. In this case, the displacement of the weight 3 is first measured, the velocity is then determined by solving differential equations of first order with respect to the displacement, and the acceleration is finally determined by solving differential equations of second order with respect to the displacement. Although a DSP (Digital Signal Processor) may be used for real-time processing, such as for the division of the interference fringes within one cycle and the calculation of the amount of shift, it is desirable to record all waveforms of light and dark signals of the interference fringes and analyze them after recorded.

Whatever kind of light wave interferometer is used, there is no difference in that the state (frequency or phase) of the reflected light from the reflecting part 9 of the weight 3 is measured. Thus, according to the present invention, the displacement, velocity, acceleration, and then inertial force of the weight 3 can be calculated with a high degree of accuracy from the state of the reflected light measured.

According to the present invention, the force, displacement and velocity are obtained at the same time by means of measuring the frequency. Therefore, not only the relationship between the force and position, but also the relationship between the force and velocity, can be determined. Using a geometrical properties of the object, stress, strain, and strain rate can be determined from force, displacement and velocity, respectively. Therefore, not only the relationship between the stress and strain, but also the relationship between the stress and strain rate, can be determined.

What is claimed is:

1. A material testing method comprising the steps of:
   attaching a weight to an object to be measured to form a mass-spring system in which the object to be measured serves as a spring element;
   applying vibration to the mass-spring system;
   measuring an inertial force acting on the weight and an displacement of the weight; and
   evaluating mechanical properties of the object to be measured based on the inertial force and displacement.

2. The method according to claim 1, wherein a light wave interferometer, which launches measurement light at a reflecting part provided on the weight and measures the state of the reflected light from the reflecting part, is used to determine the displacement and acceleration of the weight from the state of the reflected light measured, and the inertial force of the weight is calculated from the acceleration of the weight determined.

3. The method according to claim 1, wherein the weight is supported by a pneumatic linear bearing.

4. The method according to claim 2, wherein the weight is supported by a pneumatic linear bearing.

5. The method according to claim 1, wherein an actuator is coupled to the object to be measured, and vibration is applied to the mass-spring system by the actuator.

6. The method according to claim 2, wherein an actuator is coupled to the object to be measured, and vibration is applied to the mass-spring system by the actuator.

7. The method according to claim 3, wherein an actuator is coupled to the object to be measured, and vibration is applied to the mass-spring system by the actuator.

8. The method according to claim 4, wherein an actuator is coupled to the object to be measured, and vibration is applied to the mass-spring system by the actuator.

* * * * *